United States Patent [19]

Gassman et al.

[11] Patent Number: 4,699,987
[45] Date of Patent: Oct. 13, 1987

[54] (PERFLUOROALKYL)-CYCLOPEN-TADIENYLTHALLIUM

[75] Inventors: Paul G. Gassman, St. Paul; Charles H. Winter, Minneapolis, Minn.

[73] Assignee: Regents of the University of Minnesota, Minneapolis, Minn.

[21] Appl. No.: 870,098

[22] Filed: Jun. 3, 1986

[51] Int. Cl.⁴ .............................................. C07F 5/06
[52] U.S. Cl. ........................................ 556/1; 556/47; 556/53; 556/144
[58] Field of Search ........................................... 556/1

[56] References Cited

U.S. PATENT DOCUMENTS

| 2,831,007 | 4/1958 | Meister | 556/1 |
| 2,969,382 | 1/1961 | Mangham | 556/1 X |
| 3,152,157 | 10/1964 | Shapiro et al. | 556/1 X |
| 3,328,440 | 6/1967 | Shapiro et al. | 556/1 |
| 3,426,052 | 2/1969 | Hubel et al. | 556/1 |

OTHER PUBLICATIONS

P. G. Gassman et al., *Organometallics*, 2, 1470 (1983).
B. G. Conway et al., *Oranometallics*, 4, 688 (1985).
H. Bonnemann, *Angew. Chem. Int. Ed. Engl.*, 24, 248, 250 (1985).
D. W. Macomber et al., *Advances in Organometallic Chemistry*, 21, 4–28 (1982).
T. Olsson et al., *Acta Chemica Scandinavica*, B32, 293 (1978).

*Primary Examiner*—Helen M. S. Sneed
*Attorney, Agent, or Firm*—Merchant, Gould, Smith, Edell, Welter & Schmidt

[57] ABSTRACT

Perfluoroalkylcyclopentadienylthallium compounds of the general formula:

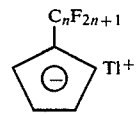

wherein n=1–5 are disclosed which are useful to modify the properties of transition metal complexes by the introduction of an electron-withdrawing perfluoroalkylcyclopentadienyl moiety thereinto.

2 Claims, 1 Drawing Figure

(PERFLUOROALKYL)-CYCLOPENTADIENYL-THALLIUM

The present invention was made with the assistance of Grant No. CHE 8414359, awarded by the National Science Foundation. The Government has certain rights in the invention.

BACKGROUND OF THE INVENTION

Since the discovery of the first cyclopentadienyl transition metal compound, ferrocene, considerable effort has been expended to evaluate the effects of substituents located on the cyclopentadienyl moiety (Cp) on the electronic character of the transition metals complexed thereto. In terms of substituents, most attention has been devoted to the pentamethylcyclopentadienyl moiety. By comparison, relatively little is known about the properties of transition metal complexes incorporating cyclopentadienyl ligands bearing electron-withdrawing substituents. See D. W. Macomber, et al., *Functionally Substituted Cyclopentadienyl Metal Compounds, Advances in Organometallic Chemistry*, 21 (1982) at pages 4-28.

Although the preparation of trifluoromethylcyclopentadienyl(cyclooctadienyl)cobalt from a halotris(-triorganophosphine)cobalt(I) complex has been reported, the trifluoromethylcyclopentadienyl ligand has not been further developed as a transition metal ligand. This is surprising, in view of the desirability of the use of cyclopentadienyl complexes which include electron-withdrawing substituents in certain catalytic processes. For example, the ability of a series of (cyclopentadienyl)(cyclooctadienyl)cobalt complexes to catalyze pyridine and/or xylene ring formation from a mixture of ethylcyanide and propyne was found to increase as the electron-withdrawing strength of the substituent on the cyclopentadienyl ring increased. Increased electron density at the cobalt atom resulted in a reduction of the catalyst activity of the cobalt complex. In contrast, electron-withdrawing substituents lowered the electron density at the cobalt atom, and the deshielded cobalt "core" exhibited higher catalytic activity. Thus, in this series, the pentamethylcyclopentadienyl system exhibited the lowest catalytic activity in the test reaction, whereas the highest activity at 65% propyne conversion was found for the benzoylcyclopentadienyl system, which was 1,000 times more reactive. See H. Bonnemann, *Angew. Chem. Int. Ed. Engl.*, 24, 248 (1985).

Therefore, a need exists for new cyclopentadienyl transition metal complexes having electron-withdrawing substituents on the cyclopentadienyl ring, and for intermediates useful for the preparation thereof.

BRIEF DESCRIPTION OF THE INVENTION

The present invention is directed to a composition of matter comprising a perfluoro($C_1$–$C_5$)alkylcyclopentadienylthallium. These compounds can be represented by the general formula I:

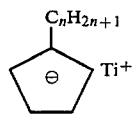

I wherein n=1-5. A preferred embodiment of the present invention is trifluoromethylcyclopentadienylthallium (I, n=1). Other compounds within the scope of the present invention include pentafluoroethylcyclopentadienylthallium, heptafluoropropylcyclopentadienylthallium, nonafluorobutylcyclopentadienylthallium and undecafluoropentylcyclopentadienylthallium; as well as the perfluoroalkyl isomers thereof.

Compounds of formula I are useful to prepare perfluoro($C_1$–$C_5$)alkylcyclopentadienide complexes of various transition metals, including complexes of iron, titanium, manganese, rhodium and iridium. The perfluoroalkyl moiety has been found to exert a powerful electron-withdrawing effect on the complexed transition metal. For example, in the case of titanocene dichloride ($Cp_2TiCl_2$), the substitution of one trifluoromethyl group ($CF_3$—) on one cyclopentadienyl ring provided a change of +0.4 eV in the Ti($2p_{3/2}$) binding energy.

Since, as discussed hereinabove, cyclopentadienyl transition metal complexes can become more reactive with respect to the catalysis of certain reactions as the electron density of the metal is reduced, it is expected that compounds of the formula I will yield perfluoro($C_1$–$C_5$)alklcyclopentadienide transition metal complexes which will possess enhanced abilities to catalyze a variety of useful reactions, and such cyclopentadienide complexes are also within the scope of the present invention. For example, the polymerization of ethylene in a Ziegler-Natta-type polymerization reaction was promoted by the use of monotrifluoromethyl-substituted titanocene dichloride [$CF_3Cp(Cp)TiCl_2$] which is prepared from trifluoromethylcyclopentadienylthallium and cyclopentadienyltitanium dichloride as described hereinbelow.

DETAILED DESCRIPTION OF THE INVENTION

Figure 1:
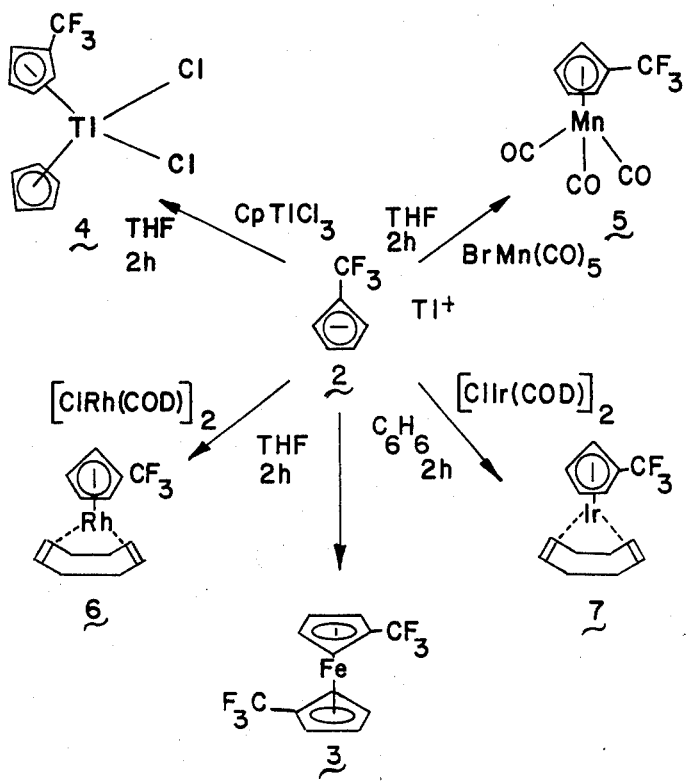
FIG. 1 is a schematic depiction of the synthesis of certain trifluoromethylcyclopentadienide transition metal complexes employing trifluoromethylcyclopentadienylthallium (2).

Compounds of formula I can be prepared by the reaction of the corresponding perfluoroalkylcyclopentadienes with thallous ethoxide (Aldrich Chemical Co., Milwaukee, WI) at about 0° C. to −20° C. in an ethereal solvent for about 5-60 min. The resultant perfluoroalkylcyclopentadienylthallium salt precipitates from the reaction mixture and can be collected by filtration and dried in vacuo.

Perfluoroalkylcyclopentadienes can be prepared by the reaction of nickelocene (Aldrich Chemical Co.) and the corresponding perfluoroalkyl iodide in the presence of triphenylphosphine in ether under ambient conditions. For example, trifluoromethylcyclopentadiene (1) was prepared in this manner according to the method of T. Olsson, et al., *Acta Chemica Scand.*, B32, 293 (1978), the disclosure of which is incorporated by reference herein.

Trifluoromethylcyclopentadienylthallium (2) was prepared by the reaction of compound 1 with thallous ethoxide at −10° C. to −15° C. in diethyl ether, as depicted in Scheme 1, below.

Scheme 1

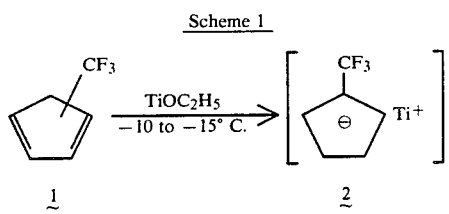

Compound 2 was unstable and decomposed rapidly at ambient temperatures. Therefore, compound 2 was used to prepare trifluoromethylcyclopentadienide transition metal complexes 3–7 without further purification, as depicted in FIG. 1.

For example, the reaction of two molar equivalents of compound 2 with one molar equivalent of ferrous chloride in tetrahydrofuran at ambient temperature for 5 hours (h) afforded bis(trifluoromethyl)ferrocene (3) in 43% yield, mp 39°–40° C. Measurements on compound 3 by x-ray photoelectron spectroscopy (XPS or ESCA) showed a Fe($2p_{3/2}$) binding energy of 708.6±0.1 eV. Comparison of this value to the values of 708.0±0.1 and 707.1±0.1 eV determined for ferrocene and decamethylferrocene, respectively, [P. G. Gassman, et al., *Organometallic*, 3, 385 (1984)], illustrates the strong electron-withdrawing effect which the presence of the trifluoromethyl group exerts on the binding energy of the inner shell electrons of iron.

An analogous comparison can be made for electronic properties of the corresponding valence shell electrons of the complexed metal. Electrochemical oxidation of 3 gave an $E°=0.95\pm0.02$ V. Comparison of this value to $E°=0.31$ V and $E°=-0.23$ V for ferrocene and decamethylferrocene, respectively, confirms that the trifluoromethyl group has an effect on the valence shell electrons of ferrocene which shifts its $E°$ by 0.64 V. This is opposite to and greater than the 0.54 V change observed for the addition of ten methyls to the cyclopentadienyl rings of ferrocene. Thus, the trifluoromethyl group, while exerting relatively little steric effect, provides a substantial electron-withdrawing electronic effect.

To illustrate the synthetic versatility of compound 2, reactions were carried out with derivatives of iron, titanium, rhodium, iridium, and manganese, as illustrated in FIG. 1. Treatment of cyclopentadienyltitanium trichloride (Aldrich Chemical Co.) in tetrahydrofuran with 1.1 equiv. of 2 gave 84% of 4, mp 141°–142° C. Examination of the ESCA spectrum of 4 showed a Ti($2p_{3/2}$) binding energy of 457.3±0.1 eV. This was compared with a related value of 456.9±0.1 eV for titanocene dichloride. Again, the strong electron-withdrawing characteristics of the trifluoromethyl group were confirmed.

Reaction of manganese pentacarbonyl bromide with compound 2 in tetrahydrofuran for 2 hours gave a 71% yield of compound 5. Similarly, reaction of chloro(1,5-cyclooctadiene)rhodium (I) dimer with 2 in tetrahydrofuran for 2 hours afforded a 71% yield of compound 6, mp 45°–46° C. Reaction of chloro(1,5-cyclooctadiene)iridium (I) dimer with compound 2 under similar conditions gave 76% of compound 7, mp 43°–44° C.

These examples amply demonstrate the versatility of trifluoromethylcyclopentadienylthallium (2) as a reagent for preparing trifluoromethylcyclopentadienyl derivatives of a variety of transition metals.

In summary, the trifluoromethyl group was found to exert a strong electron-withdrawing effect on the metal core of compounds 3–7. Therefore, it is believed that the perfluoroalkylcyclopentadienylthallium compounds of formula I will be useful intermediates for the modification of the reactive properties of a variety of transition metal complexes.

The invention will be described by reference to the following detailed examples.

Methods

The ESCA measurements described hereinabove were determined on a Physical Electronics Industries, Inc. ESCA-Auger-SIMS system equipped with a Model 15-720 Specimen Introduction/Reaction Chamber, utilizing Mg K$\alpha$ radiation. Samples were run on a polyethylene backing, and each sample was calibrated against the C(ls) binding energy (284.6 eV) The C(ls) binding energy of polyethylene was referenced to a gold standard. "PHI Handbook of X-Ray Photoelectron Spectroscopy", Muilenberg, G. E., Ed.; Perkin-Elmer Corp.: Physical Electronics Division, Eden Prairie, MN, 1979. Oxidation potentials ($E_{\frac{1}{2}}$) were evaluated by single sweep cyclic voltammetry at 22° C. with solutions which were ca. $10^{-3}$M in substrate. Scan rates were 100 mV/s. A saturated NaCl-SCE was used as the reference electrode, and a platinum bead was the working electrode. The supporting electrolyte was 0.1N tetra-n-butylammonium perchlorate. Potentials were referred to the ferrocene/ferricenium couple ($E°=0.31$ V by definition).

EXAMPLE I

Trifluoromethylcyclopentadienylthallium (2).

To a solution of trifluoromethylcyclopentadiene in diethyl ether (ca. 26 mmol) at $-10°$ C. to $-15°$ C. was added thallous ethoxide (1.9 ml; 27 mmol) via syringe. The resultant solution was stirred for 15 min, and then the solid precipitate was collected on a fine frit. The residue was washed with 20 ml of diethyl ether and vacuum-dried to affort 5.2 g of 2 (58% yield) as an off-white solid. The product was thermally unstable, and was used in the examples infra without further purification.

EXAMPLE II

Bis($\eta^5$-trifuloromethylcyclopentadienyl)iron (3).

In a 100-ml Schlenk flask was placed trifluoromethylcyclopentadienylthallium (2) (2.4 g; 7.1 mmol), iron (II) chloride (0.6 g; 4.7 mmol), and 20 ml of tetrahydrofuran. The reaction mixture was stirred for 2 hours, and then the solvent was removed under reduced pressure. The residue was triturated with 20 ml of hexane, and the mixture was applied to a 10 cm column of basic alumina. A bright yellow band was eluted with diethyl ether. Removal of the solvent under reduced pressure afforded 0.494 g (43% yield) of 3 as an orange-yellow solid: mp (sealed tube) 39°–40° C.; IR (KBr) 3020, 2975, 2840, 1733, 1489, 1456, 1388, 1305, 1230, 1146, 1125, 1111, 1030, 1020, 891, 831, 750, 727, 695 cm$^{-1}$; $^1$H NMR (CDCl$_3$) $\delta$4.58 (t, J=2 Hz, 4H), 4.40 (d, J=2 Hz, 4H); —C NMR (CDCl$_3$), 126.18 (q, $J_{CF}$=268 Hz), 79.15 (q, $J_{CCF}$=39 Hz), 71.14 (s), 68.13 (s); mass spectrum: m/e calcd. for C$_{12}$H$_8$F$_6$Fe, 321,9880; found, 321.9880. Anal. Calcd for C$_{12}$H$_8$F$_6$Fe: C, 44.76; H, 2.50. Found: C, 44.95; H, 2.55.

EXAMPLE III ($\eta^5$-Trifluoromethylcyclopentadienyl)-($\eta^4$-1,5-cyclooctadiene)rhodium (6).

In a 50-ml Schlenk flask was placed trifluoromethylcyclopentadienylthallium (2) (0.23 g; 0.68 mmol), chloro($\eta^4$-1,5-cyclooctadiene rhodium dimer (0.105 g; 0.214 mmol) (Strem Chemicals, Inc., Newburyport, MA), and 20 ml of tetrahydrofuran. The resultant mixture was stirred for 2 hours. The volatiles were then removed under reduced pressure, and the residue was triturated with 20 ml of hexane. Filtration, followed by removal of the solvent and sublimation at 70° C. (0.1 mm) afforded 0.105 g (71% yield) of 6 as a bright yellow solid: mp (sealed tube) 45°–46° C.; IR (KBr) 3000, 2945, 2880, 2835, 1735, 1495, 1458, 1436, 1395, 1332, 1307, 1246, 1235, 1147, 1121, 1094, 1065, 1055, 1031, 1025, 971, 895, 876, 835, 819, 786, 728, 700 cm$^{-1}$; $^1$H NMR (CDCl$_3$) $\delta$4.16 (s, 4H), 4.00 (s, 4H), 2.00 (m, 8H); $^{13}$C NMR (CDCl$_3$) $\delta$124.40 (q, $J_{CF}$=268 Hz), 95.76 (d or q, $J_{CCF}$=38 Hz; $J_{Rh-C}$=4.0 Hz), 88.45 (d, $J_{Rh-C}$=3.4 Hz), 84.85 (d, J=2.8 Hz), 65.23 (d, $J_{Rh-C}$=4.2 Hz), 32.17 (s); mass spectrum m/e calcd. for C$_{14}$H$_{16}$F$_3$Rh, 344.0259; found, 344.0258.

Anal. Calcd for C$_{14}$H$_{16}$F$_3$Rh: C, 48.86; H, 4.68.
Found: C, 49.14; H, 4.83.

EXAMPLE IV ($\eta^5$-Trifluoromethylcyclopentadienyl)-($\eta^4$-1,5-cyclooctadiene)iridium (7).

In a 50-ml Schlenk flask was placed trifluoromethylcylcopentadienylthallium (2) (0.30 g; 0.89 mmol), chloro($\eta^4$-1,5-cyclooctadiene)iridium dimer (0.203 g; 0.302 mmol) (Strem Chemicals, Inc.), and 10 ml of benzene. The mixture was stirred for 2 hours, and then the volatiles were removed under reduced pressure. The residue was triturated with 20 ml of hexane, and filtered to yield a clear, colorless solution. Removal of the solvent, followed by sublimation at 100° C. (0.1 mm) afforded 0.200 g (76% yield) of 7 as a white crystalline solid: mp (sealed tube) 43°–44° C.; IR (KBr) 3110, 3085, 2950, 2920, 2915, 2820, 1491, 1395, 1304, 1164, 1155, 1120, 1106, 1032, 921, 806, 729 cm$^{-1}$; $^1$H NMR (CDCl$_3$)$\delta$5.21 (d, 4H), 3.82 (s, 4H), 1.82 (m, 8H); $^{13}$C NMR (CDCl$_3$) $\delta$124.06 (q, $J_{CF}$=268 Hz), 89.26 (q, $J_{CCF}$=38 Hz), 84.59 (s), 79.46 (s), 48.82 (s), 33.57 (s); mass spectrum m/e calcd. for C$_{14}$H$_{16}$F$_3$Ir, 434.0834; found, 434.0839.

Anal. Calcd for C$_{14}$H$_{16}$F$_3$Ir: C, 38.79; H, 3.72.
Found: C, 38.95; H, 3.72.

EXAMPLE V ($\eta^5$-Trifluoromethylcyclopendienyl)manganese tricarbonyl (5)

In a 100-ml Schlenk flask was placed pentacarbonylmanganese bromide (0.996 g; 3.62 mmol) Strem Chemicals, Inc.), trifluoromethylcyclopentadienylthallium (2) (1.5 g; 4.4 mmol), and 20 ml of tetrahydrofuran. The reaction mixture was stirred at room temperature for 24 hours, and then the volatiles were removed under reduced pressure. The residue was triturated with 10 ml of pentane, and this was applied to a 10 cm column of basic alumina. A dark orange band was eluted with pentane. Removal of the solvent, followed by molecular distillation at 25° C. (0.05 mm) afforded 0.704 g (71% yield) of 5 as an orange oil: IR (KBr) 3130, 2030 (s), 2010 (sh), 1942 (vs), 1501, 1422, 1386, 1372, 1322, 1240, 1161, 1135, 1123, 1066, 1043, 1025, 898, 840, 733, 696 cm$^{-1}$; $^1$H NMR (CDCl$_3$) $\delta$5.0 (bs, 2H), 4.6 (bs, 2H); $^{13}$C NMR (CDCl$_3$) $\delta$222.67 (s), 123.28 (q, $J_{CF}$=269 Hz), 90.10 (q, $J_{CCF}$=40 Hz), 84.08 (s), 81.93 (s); mass spectrum m/e calcd. for C$_9$H$_4$O$_3$F$_3$Mn, 271.9493; found, 271.9493.

Anal. Calcd for C$_9$H$_4$O$_3$F$_3$Mn: C, 39.73; H, 1.48.
Found: C, 39.40; H, 1.47.

EXAMPLE VI ($\eta^5$-Trifluoromethylcyclopentadienyl)-($\eta^5$-cyclopentadienyl)titanium Dichloride (4).

In a 100-ml Schlenk flask was placed trifluoromethylcyclopentadienylthallium (2) (1.40 g; 4.15 mmol), cyclopentadienyltitanium trichloride (0.82 g; 3.74 mmol) (Aldrich Chemical Co.), and 20 ml of benzene. The mixture was stirred for 5 hours, and the volatiles were then removed under reduced pressure. The residue was triturated with 20 ml of methylene chloride, filtered, and the filtrate concentrated. Crystallization was induced by addition of hexane to afford 0.997 g (84% yield) of 4 as a red-orange solid: mp (sealed tube) 141°–142° C.; IR (KBr) 3115, 3035, 2930, 2855, 1736, 1512, 1502, 1450, 1392, 1335, 1249, 1170, 1137, 1122, 1074, 1059, 1020, 901, 821, 795, 735, 699, 680 cm$^{-1}$; $^1$H NMR (CDCl$_3$) $\delta$6.97 (t, J=2.9 Hz, 2H), 6.69 (s, 5H), 6.52 (t, J=2.9 Hz, 2H); $^{13}$C NMR (CDCl$_3$) $\delta$121.81 (s), 121.68 (q, $J_{CF}$=270 Hz), 121.49 (s), 119.11 (s), 116.33 (q, $J_{CCF}$=39 Hz); mass spectrum m/e calcd. for C$_{11}$H$_9$C$_2$F$_3$Ti; 315.9513; found, 315.9539.

Anal. Calcd for C$_{11}$H$_9$Cl$_2$F$_3$Ti: C, 41.68; H. 2.86.
Found: C, 41.71; H, 3.02.

The invention has been described with reference to various specific and preferred embodients and techniques. However, it should be understood that many variations and modifications may be made while remaining within the spirit and the scope of the invention.

What is claimed is:

1. A composition of matter comprising perfluoro(C$_1$–C$_5$)alkylcyclopentadienylthallium.

2. The composition of claim 1 comprising trifluoromethylcyclopentadienylthallium.

* * * * *

UNITED STATES PATENT AND TRADEMARK OFFICE
CERTIFICATE OF CORRECTION

PATENT NO. : 4,699,987

DATED : October 13, 1987

INVENTOR(S) : P. G. Gassman

It is certified that error appears in the above-identified patent and that said Letters Patent is hereby corrected as shown below:

At Col. 1, line 39, for "catalyst activity of" read --catalytic activity of--.

At Col. 1, line 61, for "$C_nH_{2n+1}$" read --$C_nF_{2n+1}$--.

At Col. 1, line 63, for "$Ti^+$" read --$Tl^+$--.

At Col. 2, line 22, for "perfluoro(C-" read --perfluoro($C_1$---.

At Col. 2, line 23, for "$_1-C_5$)alklcyclopentadienide" read --$C_5$)alkylcyclopentadienide--.

At Col. 3, line 27, for "ganometallic, 3," read --ganometallics, 3,--.

At Col. 4, line 48, for "Bis($\eta^5$-Trifuloromethylcyclopentadienyl)iron" read --Bis($\eta^5$-Trifluoromethylcyclopentadienyl)iron--.

At Col. 4, line 64, for "4H);--C NMR" read --4H); $^{13}C$ NMR--.

UNITED STATES PATENT AND TRADEMARK OFFICE
CERTIFICATE OF CORRECTION

PATENT NO. : 4,699,987
DATED : October 13, 1987
INVENTOR(S) : P. G. Gassman

It is certified that error appears in the above-identified patent and that said Letters Patent is hereby corrected as shown below:

At Col. 5, line 7, for "ro($\eta^4$-1,5-cyclooctadiene rhodium" read --ro($\eta^4$-1,5-cyclooctadiene)rhodium--.

At Col. 5, line 33, for "cylcopentadienylthallium (2)" read --cyclopentadienylthallium (2)--.

At Col. 5, line 52, for "($\eta^5$-Trifluoromethylcyclopendienyl)-manganese" read --($\eta^5$-Trifluoromethylcyclopentadienyl)-manganese.

At Col. 5, line 56, before "Strem Chemi-" insert --(--.

At Col. 6, line 43, for "$C_{11}H_9C_2F_3Ti$;" read --$C_{11}H_9Cl_2F_3Ti$;--.

At Col. 6, line 47, for "preferred embodients" read --preferred embodiments--.

At Col. 6, line 52, for "perfluoro(C-", read --perfluoro($C_1$---.

At Col. 6, line 53, for "$_1$-$C_5$)alkylcyclopentadienylthallium." read --$C_5$)alkylcyclopentadienylthallium.--.

Signed and Sealed this

Fifth Day of April, 1988

Attest:

DONALD J. QUIGG

Attesting Officer

Commissioner of Patents and Trademarks